(12) United States Patent
Baik et al.

(10) Patent No.: US 10,822,324 B2
(45) Date of Patent: Nov. 3, 2020

(54) METHOD FOR SEPARATING PROPYLENE CARBONATE IN PREPARING PROCESS OF POLYETHER CARBONATE POLYOL

(71) Applicants: POSCO, Pohang-si, Gyeongsangbuk-do (KR); Research Institute of Industrial Science & Technology, Pohang-si, Gyeongsangbuk-do (KR)

(72) Inventors: Joon-Hyun Baik, Pohang-si (KR); Jae-Hee Ha, Pohang-si (KR)

(73) Assignees: POSCO, Pohang-si (KR); RESEARCH INSTITUTE OF INDUSTRIAL SCIENCE & TECHNOLOGY, Pohang-si (KR)

( * ) Notice: Subject to any disclaimer, the term of this patent is extended or adjusted under 35 U.S.C. 154(b) by 0 days.

(21) Appl. No.: 16/469,812

(22) PCT Filed: Dec. 15, 2017

(86) PCT No.: PCT/KR2017/014844
§ 371 (c)(1),
(2) Date: Jun. 14, 2019

(87) PCT Pub. No.: WO2018/111036
PCT Pub. Date: Jun. 21, 2018

(65) Prior Publication Data
US 2019/0315706 A1 Oct. 17, 2019

(30) Foreign Application Priority Data

Dec. 16, 2016 (KR) .................. 10-2016-0172931

(51) Int. Cl.
*C07D 317/36* (2006.01)
*B01D 11/04* (2006.01)
*C08G 64/34* (2006.01)
*C08G 64/40* (2006.01)

(52) U.S. Cl.
CPC .......... *C07D 317/36* (2013.01); *B01D 11/048* (2013.01); *C08G 64/34* (2013.01); *C08G 64/406* (2013.01)

(58) Field of Classification Search
CPC .................................................... C07D 317/36
USPC .......................................................... 549/230
See application file for complete search history.

(56) References Cited

U.S. PATENT DOCUMENTS

| 4,721,818 | A | 1/1988 | Harper et al. |
| 5,416,241 | A | 5/1995 | Ruszkay |
| 2008/0021154 | A1 | 1/2008 | Haider et al. |
| 2009/0203875 | A1 | 8/2009 | Suzuki et al. |
| 2010/0048935 | A1 | 2/2010 | Mijolovic et al. |
| 2016/0194441 | A1 | 7/2016 | Blanco Gonzalez et al. |
| 2019/0010284 | A1 | 1/2019 | Baik et al. |

FOREIGN PATENT DOCUMENTS

| JP | H07-238161 A | 9/1995 |
| JP | 2538302 B2 | 9/1996 |
| KR | 10-2005-0019173 A | 3/2005 |
| KR | 10-2009-0032086 A | 3/2009 |
| KR | 10-2009-0107555 A | 10/2009 |
| KR | 10-2010-0094581 A | 8/2010 |
| KR | 10-2016-0042967 A | 4/2016 |
| KR | 10-1736639 B1 | 5/2017 |
| KR | 10-1867721 B1 | 6/2018 |
| KR | 10-1908864 B1 | 12/2018 |
| WO | 2014/108517 A2 | 7/2014 |

OTHER PUBLICATIONS

Extended European Search Report dated Aug. 27, 2019 issued in European Patent Application No. 17880054.6.
International Search Report issued in corresponding International Patent Application No. PCT/KR2017/014844 dated Apr. 12, 2018.

*Primary Examiner* — Taofiq A Solola
(74) *Attorney, Agent, or Firm* — Morgan, Lewis & Bockius LLP

(57) ABSTRACT

The present invention relates to a method for selectively separating propylene carbonate by adding water to reaction products comprising a polyether carbonate polyol and propylene carbonate, which are generated from a polymerization reaction of propylene oxide and carbon dioxide under a double metal cyanide (DMC) catalyst, wherein an economical and effective separation of propylene carbonate can be achieved.

4 Claims, 1 Drawing Sheet

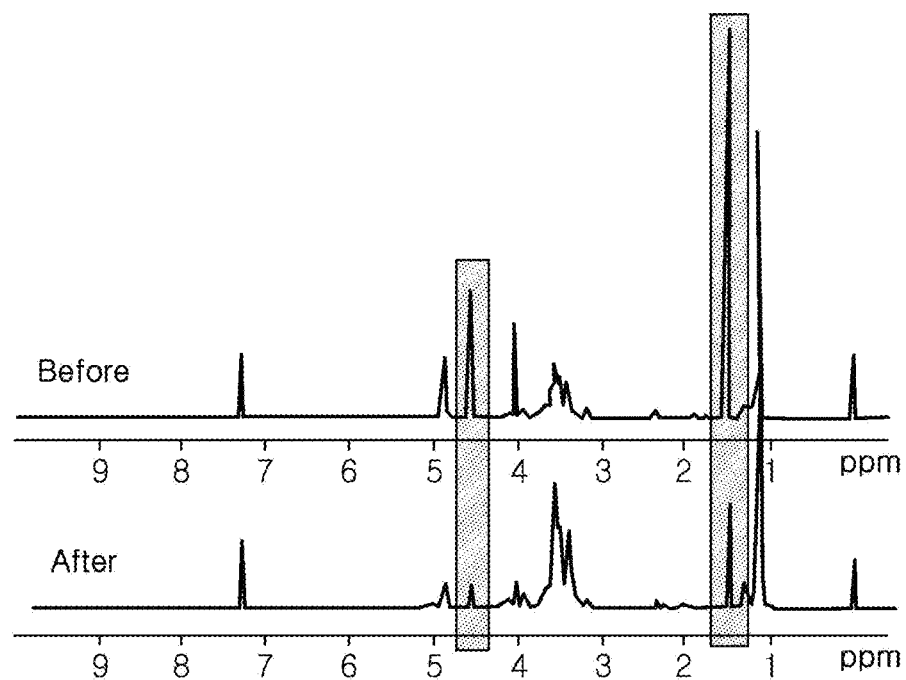

METHOD FOR SEPARATING PROPYLENE CARBONATE IN PREPARING PROCESS OF POLYETHER CARBONATE POLYOL

CROSS-REFERENCE OF RELATED APPLICATIONS

This application is the U.S. National Phase under 35 U.S.C. § 371 of International Patent Application No. PCT/KR2017/014844, filed on Dec. 15, 2017, which in turn claims the benefit of Korean Patent Application No. 10-2016-0172931, filed Dec. 16, 2016, the entire disclosures of which applications are incorporated by reference herein.

TECHNICAL FIELD

The present disclosure relates to a technique for isolating propylene carbonate in a polyether carbonate polyol preparation process.

BACKGROUND ART

Polyether carbonate polyol is produced through the addition of carbon dioxide due to a polymerization reaction of propylene oxide and carbon dioxide in the presence of a double metal cyanide (DMC) catalyst, and the reaction formula thereof is as follows.

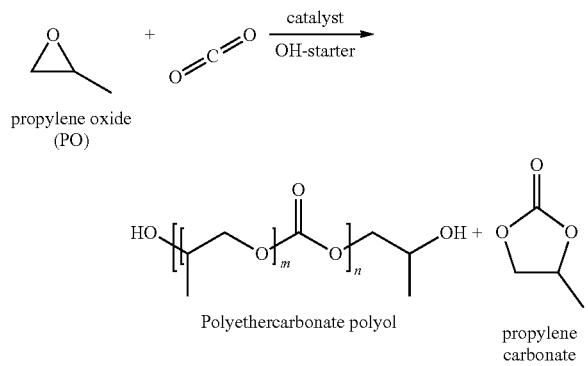

As can be seen from the reaction formula above, propylene carbonate is produced as by-product during the polymerization reaction of polyether carbonate polyol. In order to obtain high-purity polyol, it is necessary to isolate therefrom the propylene carbonate formed as by-product.

As a method of isolating such a propylene carbonate by-product, a distillation method as described in Japanese Patent Publication No. 1995-238161 may be used. However, propylene carbonate has a low vapor pressure and a high boiling point, and therefore, propylene carbonate isolation using an ordinary distillation process would require high-temperature, high-pressure steam at temperatures of 240° C. or more, thus consuming a large amount of energy and significantly reducing cost-effectiveness.

DISCLOSURE

Technical Problem

The present disclosure provides a method of effectively isolating propylene carbonate which is produced as by-product during a polyol production process, the method being energy-efficient and capable of isolating propylene carbonate without using high-temperature, high-pressure steam.

Technical Solution

The present disclosure provides a method of selectively isolating propylene carbonate by adding water to reaction products containing polyether carbonate polyol and propylene carbonate during a process of producing polyol from a reaction of propylene oxide and carbon dioxide.

Water may be added to the reaction products in a ratio of 1:1 to 10. Water is added in excess in order to completely dissolve propylene carbonate. When water is added in an excess amount, such as in an amount 10 or more times the amount of the reaction products, excessive difficulties may arise in a subsequent process, and thus it is not preferable.

It is preferable to separate a layer containing polyether carbonate and a layer containing propylene carbonate from each other after sufficiently mixing the mixture of the reaction products.

Advantageous Effects

According to the method of the present disclosure, propylene carbonate can be efficiently isolated from the mixture containing polyether carbonate and propylene carbonate without using high-temperature, high-pressure steam, thus consuming relatively less energy and being cost-effective.

DESCRIPTION OF DRAWINGS

FIG. 1 illustrates the NMR of a polyol reaction product before and after isolation of propylene carbonate according to the present disclosure.

BEST MODE FOR INVENTION

The present disclosure relates to a method of removing by-product propylene carbonate from polyether carbonate polyol which is a product from a process of producing polyether carbonate polyol through a reaction of propylene oxide and carbon dioxide in the presence of a double metal cyanide (DMC) catalyst.

Propylene carbonate, which is produced as by-product from the production process of polyether carbonate polyol, has solubility in water that is 17.5% higher at room temperature compared to that of polyether carbonate polyol. In light of the foregoing, the present disclosure aims to isolate by-product propylene carbonate from polyether carbonate polyol by exploiting the above-described difference in solubility in water.

The water used above may be distilled water but is not limited thereto.

The water is added in an excess amount to the mixture of polyether carbonate polyol and propylene carbonate, and preferably, the water is added in a volume ratio of 1:1 to 10. Considering that a small amount of propylene carbonate exists in the product, polyether carbonate polyol, adding water in an amount greater than or equal to a total volume of the polyether carbonate polyol and the propylene carbonate is sufficient to dissolve the by-product propylene carbonate. An upper limit of the amount of water being added is not particularly limited; however, for efficient operation of processes, it is preferable that water is added in an amount no more than 10 parts by volume with respect to 1 part by volume of the mixture. For example, the water may be added to the mixture of polyether carbonate polyol and propylene carbonate in a volume ratio within a range of 1:1 to 8, 1:1 to 7, and 1:1 to 5.

The water used above may be water at room temperature, and more specifically, water in a temperature range of 20° C. to 50° C.

Here, after adding water to the mixture of polyether carbonate polyol and propylene carbonate, there may be included an operation of performing sufficient stirring to allow propylene carbonate contained in polyether carbonate polyol to be dissolved in the water.

There is included an operation of isolating propylene carbonate dissolved in water from the mixture of polyether carbonate polyol and propylene carbonate. The isolation may be achieved by centrifugation. The centrifugation is subject to adjustment depending on a content of propylene carbonate contained in polyether carbonate polyol, and is not particularly limited.

By the centrifugation, the layer separation occurs between an overlying solution containing propylene carbonate dissolved in water and an underlying solution containing polyether carbonate polyol. Accordingly, by isolating and removing the overlying solution therefrom, the underlying solution can be obtained, thereby yielding a desired product, polyether carbonate polyol of high purity.

More preferably, there may be included an operation of drying the polyether carbonate polyol thus obtained. The drying is performed to remove water from the polyether carbonate polyol, and conditions under which the drying is performed are not particularly limited as long as they can cause water to evaporate.

According to the present disclosure, the method of the present disclosure can remove propylene carbonate from polyether carbonate polyol by exploiting a high solubility of propylene carbonate in water, and since the use of high-temperature, high-pressure steam is not required in the method of the present disclosure, the amount of energy consumed can be significantly reduced.

While this disclosure includes specific example embodiments, it will be apparent to those skilled in the art that various changes in form and details may be made in these example embodiments without departing from the spirit and scope of the claims and their equivalents. The examples described herein are to be considered in a descriptive sense only, and not for purposes of limitation.

BEST MODE FOR INVENTION

Hereinbelow, an example of the present disclosure will be described in greater detail. The example described below is one of many examples in which the present disclosure can be implemented and thus, the present disclosure is not defined by the example described herein.

Example 1

Reaction products, in which polyether carbonate polyol and propylene carbonates co-exist, obtained from polymerizing propylene oxide and carbon dioxide in the presence of a double metal cyanide (DMC) catalyst, were prepared.

$^1$H-NMR analysis was performed on the prepared reaction products, and the results thereof are shown in FIG. 1.

As can be seen from FIG. 1, peaks at 1.5 ppm and 4.5 ppm, corresponding to propylene carbonate, were observed in the prepared reaction products.

10-15 ml of the reaction products were placed in a centrifugation tube. Subsequently, distilled water (at room temperature) was added to fill the centrifugation tube (35-40 ml of water).

Next, the centrifugation tube was vigorously shaken, thereby thoroughly mixing the overlying solution (distilled water) with the underlying solution (organic mixture).

The thoroughly mixed mixture was centrifuged at 5,000 rpm for 15 minutes, using a centrifuge.

Once the centrifuged overlying solution was isolated, the underlying solution thus obtained was placed in a 500 mL flask. The underlying solution placed in the flask was dried under vacuum at 110° C. for four hours, using a rotary evaporator.

As a result, polyether carbonate polyol from which propylene carbonate had been isolated was obtained.

The polyether carbonate polyol thus obtained was analysed by $^1$H-NMR, and the results are shown in FIG. 1.

As can be seen from FIG. 1, it could be confirmed that the $^1$H-NMR results after isolation, peaks at 1.5 ppm and 4.5 ppm, corresponding to propylene carbonate, were significantly reduced.

The invention claimed is:

1. A method of removing propylene carbonate from a mixture containing polyether carbonate polyol and propylene carbonate, the method comprising adding water to said mixture to selectively remove propylene carbonate therefrom.

2. The method of claim 1, wherein the water is added in a volume ratio of 1:1 to 10 with respect to the mixture containing polyether carbonate polyol and propylene carbonate.

3. The method of claim 1, comprising: centrifuging the mixture having the water added thereto, to separate the mixture into an underlying solution containing polyether carbonate polyol and an overlying solution containing propylene carbonate; and isolating and removing the overlying solution therefrom to recover the polyether carbonate polyol.

4. The method of claim 3, further comprising an operation of drying the polyether carbonate polyol.

* * * * *